(12) United States Patent
Ohashi et al.

(10) Patent No.: US 7,547,815 B2
(45) Date of Patent: Jun. 16, 2009

(54) ABSORBENT PAD HAVING ZONES WITH DIFFERENT FLEXIBILITIES

(75) Inventors: Naoto Ohashi, Kagawa-ken (JP);
Tomomi Oku, Kagawa-ken (JP); Hikari Kawakami, Kagawa-ken (JP); Ryuichi Kamiyama, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 200 days.

(21) Appl. No.: 11/234,155

(22) Filed: Sep. 26, 2005

(65) Prior Publication Data

US 2006/0069371 A1 Mar. 30, 2006

(30) Foreign Application Priority Data

Sep. 30, 2004 (JP) ............................. 2004-286344

(51) Int. Cl.
*A61F 13/15* (2006.01)
*A61F 13/20* (2006.01)

(52) U.S. Cl. .................. 604/378; 604/385.01; 604/380

(58) Field of Classification Search ............ 604/385.01, 604/367, 378–380, 385.101

See application file for complete search history.

(56) References Cited

U.S. PATENT DOCUMENTS

| | | | | |
|---|---|---|---|---|
| 2,690,749 A | * | 10/1954 | Nelson | ..................... 604/398 |
| 3,559,648 A | * | 2/1971 | Mason, Jr. | ................ 604/375 |
| 3,593,717 A | * | 7/1971 | Jones, Sr. | ................... 604/365 |
| 4,762,521 A | * | 8/1988 | Roessler et al. | ....... 604/385.26 |
| 4,968,312 A | * | 11/1990 | Khan | ................... 604/385.13 |
| 4,990,147 A | * | 2/1991 | Freeland | .............. 604/385.22 |
| 5,211,641 A | | 5/1993 | Roos et al. | |
| 6,423,046 B1 | * | 7/2002 | Fujioka et al. | ........ 604/385.14 |
| 7,090,665 B2 | * | 8/2006 | Ohashi et al. | ......... 604/385.14 |
| 2006/0184151 A1 | * | 8/2006 | Onishi et al. | .......... 604/385.19 |

FOREIGN PATENT DOCUMENTS

| | | |
|---|---|---|
| EP | 0 136 524 | 4/1985 |
| JP | 10-328233 | 12/1998 |
| JP | 11-004851 | 1/1999 |
| JP | 2001-095842 | 4/2001 |

* cited by examiner

*Primary Examiner*—Michele Kidwell
(74) *Attorney, Agent, or Firm*—Lowe Hauptman Ham & Berner, LLP (57) ABSTRACT

A disposable absorbent pad includes an absorbent fibrous structure having a longitudinal axis, a transverse axis, and front and rear regions aligned with each other in a direction along the longitudinal axis. The pad has a flexibility of the front region higher than in rear region.

8 Claims, 9 Drawing Sheets

ABSORBENT PAD HAVING ZONES WITH DIFFERENT FLEXIBILITIES

RELATED APPLICATIONS

The present application is based on, and claims priority from, Japanese Application Serial Number 2004-286344, filed Sep. 30, 2004, the disclosure of which is hereby incorporated by reference herein in its entirety.

BACKGROUND OF THE INVENTION

This invention relates to an absorbent pad and more particularly to a disposable absorbent pad providing a good fit to a pad wearer's body.

Various absorbent pads of such a type have conventionally been well known, for example, a disposable absorbent pad provided on the side facing the wearer's garment with a depressed region extending in a longitudinal direction of the pad (REFERENCE 1); a disposable absorbent pad provided in a vicinity of transversely opposite side edges with a pair of regions depressed from the upper surface toward the lower surface of the pad (REFERENCE 2); or a disposable absorbent pad provided on both the side facing the wearer's body and the side facing away from the wearer's body with a plurality of grooves (REFERENCE 3). Such known disposable absorbent pads unexceptionally intend to achieve a smooth bending of the pad.

[REFERENCE 1] Japanese Unexamined Patent Application Publication No. 2003-210507
[REFERENCE 2] Japanese Unexamined Patent Application Publication No. 2000-166967
[REFERENCE 3] Japanese Unexamined Patent Application Publication No. 1998-99372

In the case of the absorbent pad disclosed in REFERENCE 1, the pad is easily bent along the depressed region so that the side of the pad facing the wearer's body may define an apex along this depressed region. However, it is unreliable that the pad could be kept in close contact with the pad wearer's body so far as the region of the pad other than the depressed region is concerned. In other words, there is an anxiety that so-called sideways leakage of bodily fluid might occur in the region of the pad being not in close contact with the wearer's body. For the absorbent pad disclosed in REFERENCE 2, it is certainly easy to be bent along the paired depressions and thereby to be deformed over the full width of the pad in an inverted U-shape. However, there is a possibility that the pad might be bent in the opposite direction to create a U-shape under a body weight of the wearer. In the case of the absorbent pad disclosed in REFERENCE 3, while the grooves form a plurality of crests adapted to come in close contact with the wearer's body as the pad is bent along the grooves, a plurality of troughs each defined between each pair of the adjacent crests cannot come in close contact with the wearer's body.

SUMMARY OF THE INVENTION

In view of the problems as have been described above, it is an object of this invention to provide an absorbent pad affording an excellent fit particularly in a region of the pad destined to come in contact with a wearer's crotch region.

The object set forth above is achieved, according to this invention, by an absorbent pad comprising an absorbent fibrous structure having a longitudinal axis, a transverse axis, a first surface, a second surface opposite to the first surface, and front and rear regions aligned with each other in a direction along the longitudinal axis, and a flexibility of the front region being higher than that of the rear region.

The flexibility of the front region may be previously adjusted in this manner to be higher than that of the rear region to ensure that the absorbent pad is more easily deformable in the front region than in the rear region. Consequentially, the front region of the absorbent pad is able to be kept in close contact with the wearer's body. The rear region is not so deformable as the front region is and therefore able to cover the wearer's body with a sufficient spatial allowance to contain solid excrement such as feces without accreting it to the wearer's body.

For the purpose of previously adjusting the front region to exhibit the flexibility which is higher than that exhibited by the rear region, the front region of the absorbent pad may be formed from materials having a relatively high flexibility and the rear region of the absorbent pad may be formed from materials having a relatively low flexibility. This purpose may be achieved also by an alternative arrangement such that the absorbent pad has a density higher in the front region than in the rear region. The same purpose may be achieved also by still another arrangement such that a first flexible pivot region extending along a longitudinal axis and paired second and third flexible pivot regions extending in the direction along the longitudinal axis so as to be spaced from the first flexible pivot region as well as from each other in the direction along the transverse axis are laid exclusively in the front region. With such an arrangement that the first, second and third flexible pivot regions are laid exclusively in the front region of the absorbent pad, it is ensured that the absorbent pad is kept in close contact with the wearer's crotch region as the pad is bent along the first flexible pivot region and in close contact with the wearer's inguinal region as the pad is bent along the paired second and third flexible pivot regions.

While the paired second and third flexible pivot regions may be substantially parallel to the first flexible pivot region for the effective operation of these flexible pivot regions, these second and third flexible pivot regions preferably describe circular arcs which are convex toward the first flexible pivot region.

The second and third flexible pivot regions may be symmetric or asymmetric about the longitudinal axis.

Preferably, the first flexible pivot region is defined by a linear through-hole and the paired second and third flexible pivot regions are defined by grooves.

The first flexible pivot region defined by the linear through-hole is effective to enlarge a surface area of the absorbent fibrous structure and thereby to improve a body fluid absorbing capacity of the absorbent pad. Transversely opposite side edges of the linear through-hole are put together into a narrow gap of the wearer's crotch region and thereby provide a good fit with respect to the wearer's crotch region as the absorbent pad is bent along the linear through-hole. With the paired second and third flexible pivot regions defined by the second and third grooves which do not extend through the thickness of the pad, the absorbent pad is gently bent along these grooves and an intermediate region of the pad extending between these second and third grooves is deformed so as to be raised on the side of the first surface. In this way, the first flexible pivot region defined by the linear through-hole cooperates with the paired second and third flexible pivot regions to provide a good fit of the absorbent pad with respect to the wearer's crotch region and inguinal region.

Shapes of the linear through-hole as well as of the paired grooves are not specified in particular and may be selected from various shapes such as rectangular and oval shapes. The paired second and third grooves may be different from each other or identical to each other in shape as well as in size. The linear through-hole and the paired grooves may extend continuously or extend intermittently.

While a dimension by which the second and third flexible pivot regions are spaced from each other may be selected depending on a crotch width of the individual wearer, such a dimension is preferably in a range of 60 to 90 mm in order that a good fit of the absorbent pad with respect to the wearer's crotch region may be provided.

In the case of the paired second and third flexible pivot regions respectively describing the circular arcs which are convex toward the first flexible pivot region, the dimension by which these second and third flexible pivot regions are spaced from each other is defined as the shortest distance between these second and third flexible pivot regions.

While a thickness dimension of the absorbent fibrous structure may be in such order that an adequate amount of bodily fluid can be absorbed and the wearer do not experience any uncomfortable feeling with the absorbent pad being put in the wearer's crotch region, this thickness dimension is preferably 1 to 10 mm and more preferably in a range of 2.5 to 10 mm. While a width dimension of the linear through-hole as measured in the direction along the transverse axis may be appropriately selected depending on the thickness dimension so that the absorbent pad may be smoothly bent, this width dimension is preferably in a range of 5 to 25 mm and more preferably in a range of 8 to 15 mm. So far as the thickness dimension of the absorbent fibrous structure as well as the width dimension of the linear through-hole is in the ranges as have been described above, it is unlikely that the transversely opposite side edges might come in contact with each other and therefore the region defined by the linear through-hole along which the absorbent pad is bent can be kept free from the presence of the absorbent fibrous structure even after the absorbent pad has been bent along the linear through-hole. Consequentially, the region with which the wearer's crotch regions come in contact is prevented from being wetted with bodily fluid and the wearer is protected from any uncomfortable feeling due to wetness of this region.

While a length dimension of the linear through-hole as measured in the direction along the longitudinal axis may be appropriately selected depending on a size of the individual absorbent pad in order that the position of the linear through-hole may be aligned with the position of the wearer's crotch region, this length dimension preferably corresponds to a range of 10 to 60%, more preferably to a range of 20 to 40% of the length dimension of the absorbent fibrous structure as measured in the dimension along the longitudinal axis.

While respective length dimensions of the paired grooves as measured in the direction along the longitudinal axis may be appropriately selected depending on a size of the individual absorbent pad in order that these paired grooves may be positioned in alignment with the position of the wearer's inguinal region, these length dimensions preferably correspond to a range of 10 to 50% of the length dimension of the absorbent pad as measured in the direction along the longitudinal axis. Within such range, the length dimensions of these paired grooves may be identical with each other or different from each other.

While the paired grooves may be depressed from the first surface or from the second surface, these paired grooves are preferably depressed from the second surface or from both the first and second surfaces in order that the absorbent pad may be smoothly deformed so as to be convex on the side of the first surface.

In the case of the paired grooves depressed from both the first surface and the second surface, the paired grooves depressed from the first surface preferably have a depth dimension which is identical with or less than a depth dimension of the paired grooves depressed from the second surface in order that the absorbent pad may be smoothly bent so as to be convex on the side of the first surface.

The absorbent fibrous structure may be a monolayer structure or multilayered structure and, when it is desired to use the multilayered structure, a two-layered structure consisting of an upper layer and a lower layer is preferable. Such absorbent fibrous structure of two-layer structure is advantageous in that, the shape as well as the size of the absorbent fibrous structure and the shapes as well as the sizes of the linear through-hole and the paired grooves on the side of the first surface can be easily made different from those on the side of the second surface.

While the length dimension and the width dimension of the linear through-hole on the side of the first surface are identical with those on the side of the second surface, the length dimension and the width dimension of the linear through-hole on the side of the first surface are preferably different from those on the side of the second surface. This is for the reason that the size of the linear through-hole as viewed from the side of the first surface of the absorbent pad can be kept substantially constant even if some misalignment occurs in the course of laminating the upper and lower layers of the absorbent fibrous structure so far as the length dimension as well as the width dimension of the linear through-hole on the side of the first surface is different from those on the side of the second surface. In this case, the length dimension as well as the width dimension of the linear through-hole on the side of the first surface may be larger than those on the side of the second surface or vice versa. Preferably, however, the length dimension of the linear through-hole on the side of the first surface is larger than that on the side of the second surface and the width dimension of the linear through-hole on the side of the first surface is larger than that on the side of the second surface in order that the absorbent pad may fit to the deepest region of the wearer's crotch region as the absorbent pad is bent.

The first surface preferably has a liquid-permeability and more preferably this first surface is formed from a liquid-permeable sheet. The second surface preferably has a hydrophobic property and more preferably this second surface is treated with a water-repellent agent or formed from a hydrophobic sheet. Thus the absorbent pad absorbs bodily fluid through the first surface and prevents bodily fluid having been absorbed from leaking out the pad.

While it is possible to form the absorbent pad from the absorbent fibrous structure alone, the absorbent pad preferably comprises the liquid-permeable sheet defining the first surface, the hydrophobic sheet defining the second surface and a liquid-absorbent core interposed between these two sheets in order to facilitate production of the absorbent pad of which the first surface has a liquid-permeability and the second surface has a hydrophobic property.

As materials used to form the liquid-permeable sheet, the hydrophobic sheet and the liquid-absorbent core, those usually used in the field of relevant art may be used without any specified limitation.

The absorbent pad according to this invention allows the front region of the absorbent pad to be easily deformed and thereby to be kept in close contact with the wearer's body so that a so-called sideways leakage of bodily fluid. In contrast with the front region, the rear region is able to cover the wearer's body with a sufficient spatial allowance to contain solid excrement such as feces without accreting it to the wearer's body.

The other arrangements and materials will be readily understood by those skilled in the art from the following description of the preferred embodiments of this invention. It should be noted that this invention is not limited to these embodiments described hereunder.

DETAILED DESCRIPTION OF THE PREFERRED EMBODIMENTS

Embodiments of this invention will be described more in details with reference to the accompanying drawings.

First Embodiment

Figure 1:
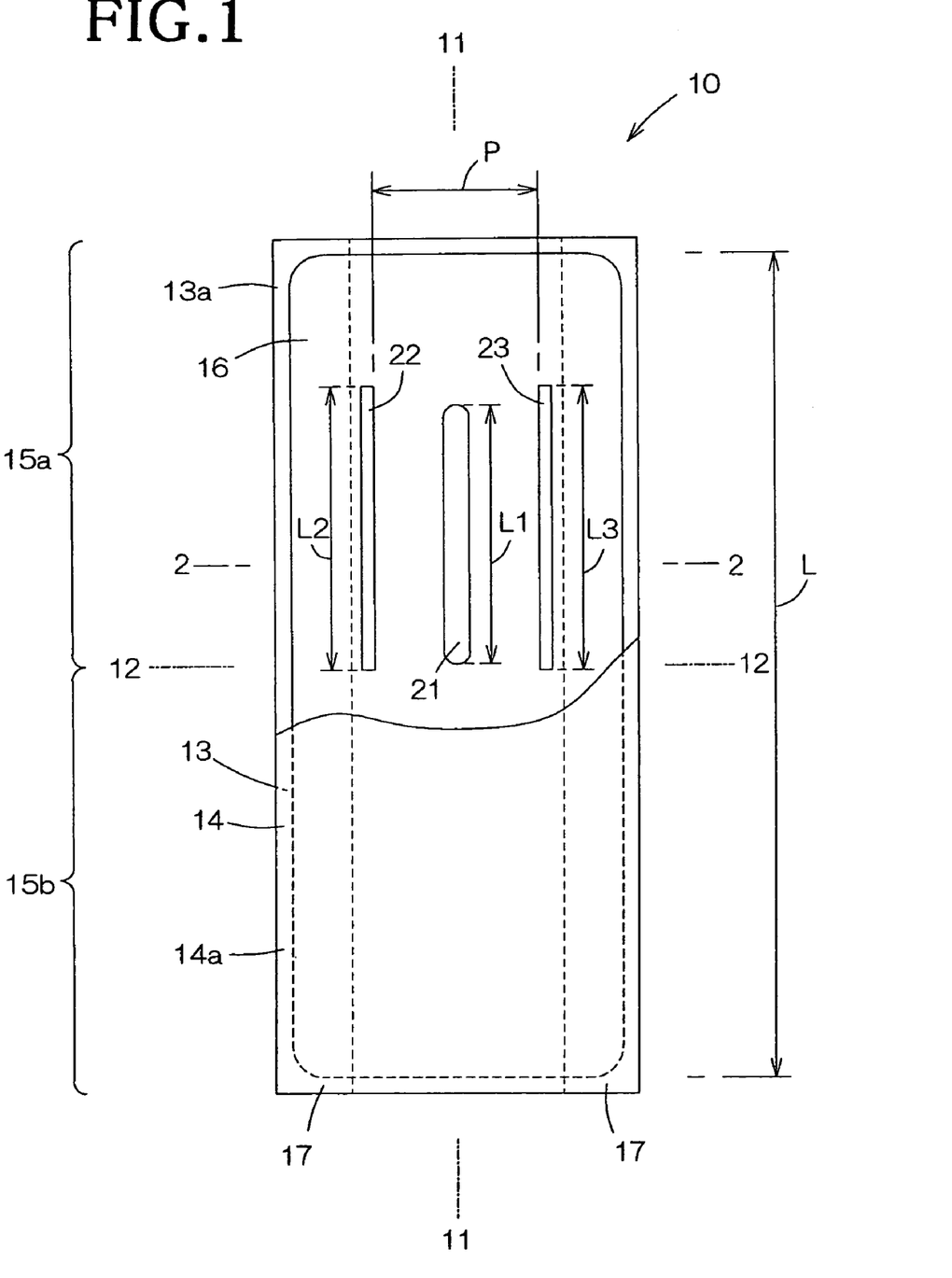
FIG. 1 is a partially cutaway plan view showing a first embodiment of the absorbent pad according to this invention.
Figure 2:
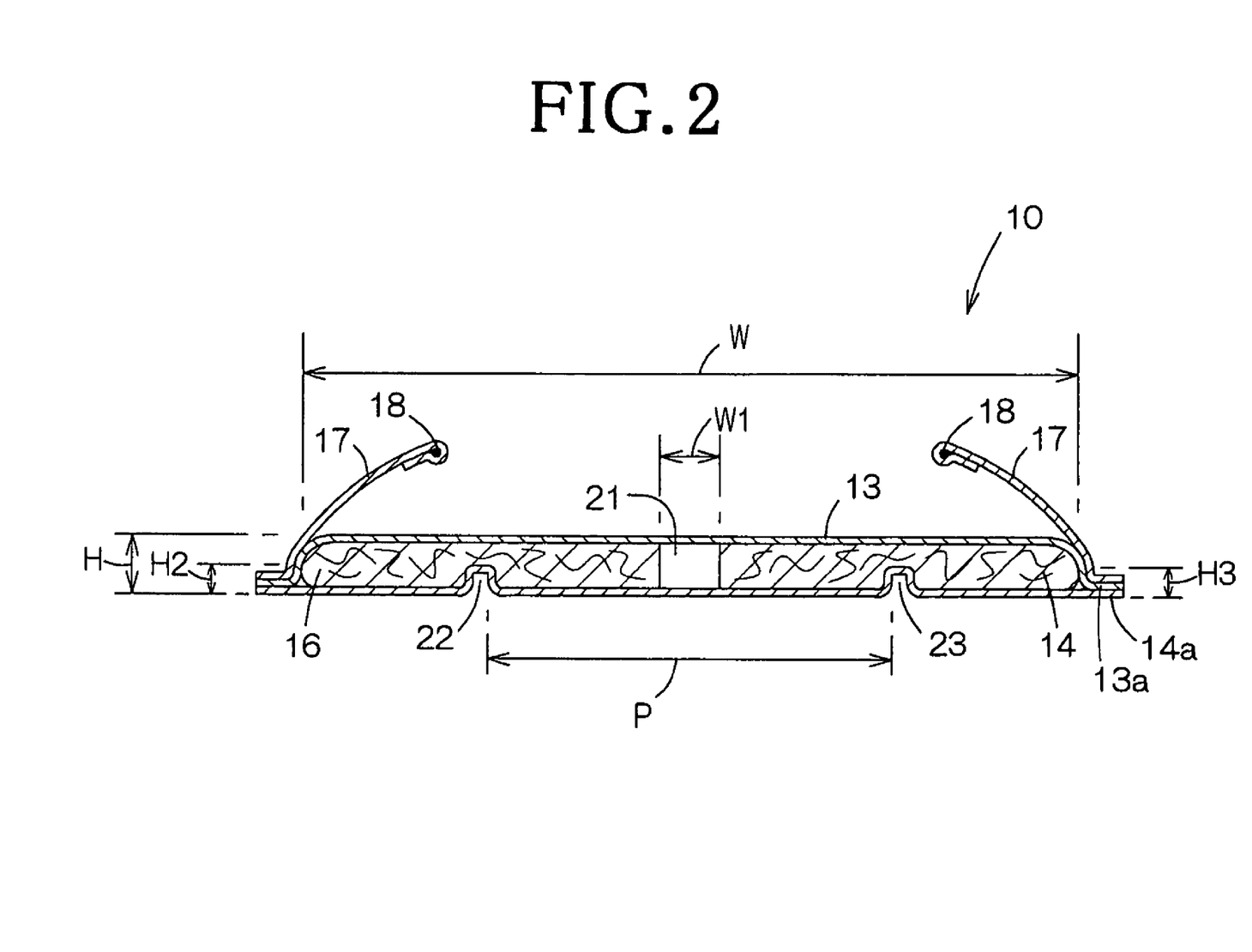
FIG. 2 is a sectional view taken along the line 2-2 in FIG. 1.
Figure 3:
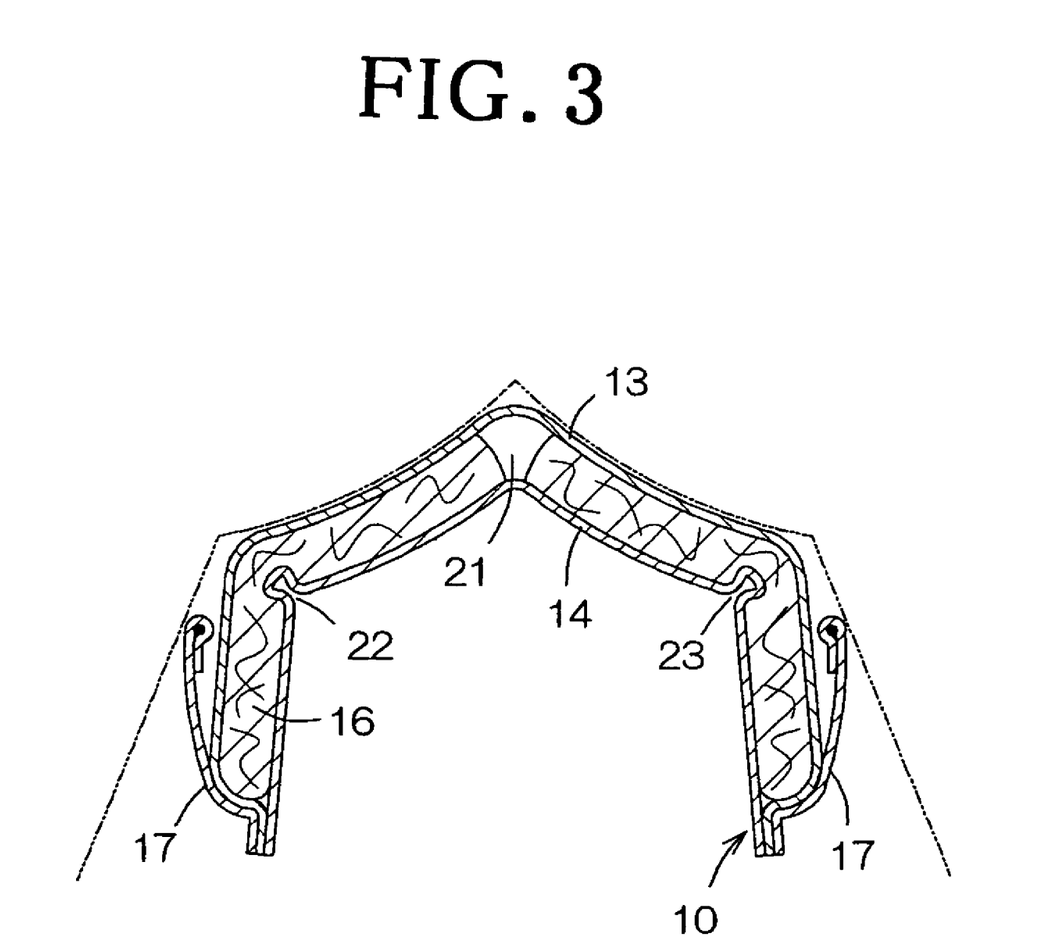
FIG. 3 is a sectional view taken along the same line as in FIG. 2 showing the first embodiment as put on the wearer's body.

FIG. 1 is a partially cutaway plan view showing a first embodiment of the absorbent pad according to this invention as viewed from its rear side, FIG. 2 is a sectional view taken along the line 2-2 in FIG. 1 and FIG. 3 is a sectional view taken along the same line as in FIG. 2, showing the first embodiment as put on the wearer's body.

As will be seen in FIG. 1, the absorbent pad includes an absorbent fibrous structure 10. The absorbent fibrous structure 10 has a longitudinal axis 11, a transverse axis 12 which is orthogonal to the longitudinal axis 11, a front surface destined to come in contact with the wearer's body, a lower surface 14 opposite to the top surface, and front and rear regions 15a, 15b which line up in a direction along the longitudinal axis 11. The absorbent fibrous structure 10 primarily comprises a liquid-permeable topsheet 13a defining the upper surface 13, a hydrophobic backsheet 14a defining the lower surface 14 and a liquid-absorbent core 16 interposed between these two sheets 13a, 14a.

The absorbent fibrous structure 10 further comprises a pair of barrier cuffs 17 extending in a longitudinal direction in a vicinity of transversely opposite side edges of the liquid-absorbent core 16. Each of the barrier cuffs 17 is bonded to the topsheet 13a at its longitudinally opposite ends and its transversely outer side edge (See FIG. 2). Each of the barrier cuffs 17 is provided along its transversely inner edge with an elastic member 18 such as a rubber strand attached in a stretched state thereto so that the barrier cuffs 17 are normally biased to rise up on the topsheet 13a (See FIG. 2).

The topsheet 13a and the backsheet 14a extend outward beyond a peripheral edge of the liquid-absorbent core 16 and are overlapped and bonded together along these extensions (See FIG. 2).

The topsheet 13a is made of a well known thermoplastic synthetic fibrous nonwoven fabric having a basis weight of about 15 to 35 $g/m^2$, preferably about 20 to 25 $g/m^2$. Thermoplastic synthetic fibers may be, for example, of polyolefin, polyester or polyamide.

The backsheet 14a is made of a well known solution-resistant thermoplastic film having a basis weight of about 10 to 30 $g/m^2$, preferably about 15 to 25 $g/m^2$. Such film may be, for example, of polyolefin-based synthetic resin.

The liquid-absorbent core 16 is formed from a mixture of fluff pulp, super-absorbent polymer particles and optionally thermoplastic synthetic fibers. A content of the super-absorbent polymer particles is in a range of 20 to 30 wt %. Though not shown, the liquid-absorbent core 16 is wrapped with a liquid-diffusive sheet such as a tissue paper and compressed to an appropriate thickness, for example, in order to protect the core 16 from undesired deformation.

The barrier cuffs 17 are made of a well known thermoplastic synthetic fibrous nonwoven fabric having a basis weight of about 10 to 25 $g\ m^2$, preferably about 15 to 20 $g/m^2$. Thermoplastic synthetic fibers may be, for example, of polyolefin, polyester or polyamide.

The liquid-absorbent core 16 has a length dimension L of 420 mm as measured in the direction along the longitudinal axis, a width dimension W of 150 mm as measured in the direction along the transverse axis and a thickness dimension H of 6.50 mm.

The absorbent pad is provided with a linear through-hole (first flexible pivot region) 21 extending along the longitudinal axis and a pair of grooves (serving as second and third flexible pivot regions, respectively) 22, 23 extending also in the direction along the longitudinal axis 11 but spaced apart from the linear through-hole 21 in the direction along the transverse axis 12. These linear through-hole 21 and paired grooves 22, 23 are provided exclusively in the front region 15a. In other words, approximately half of the absorbent pad having the linear through-hole 21 and the paired grooves 22, 23 corresponds to the front region 15a and the remainder defines the rear region 15b.

As will be apparent from FIG. 2, the liquid-absorbent core 16 is absent in the linear through-hole 21.

A length dimension L1 of the linear through-hole 21 as measured in the direction along the longitudinal axis 11 is about 120 to 140 mm, preferably about 125 to 135 mm which corresponds to about 30% of the length dimension L of the liquid-absorbent core 16 as measured in the direction along the longitudinal axis 11. A width dimension W1 of the linear through-hole 21 as measured in the direction along the transverse axis is about 8 to 16 mm, preferably about 10 to 14 mm.

The topsheet 13a and the backsheet 14a may flatly extend so as to define the upper and lower surfaces 13, 14, respectively, and to cover the linear through-hole 21 as seen in FIG. 2 or these top- and backsheets 13a, 14a may extend along a contour of the liquid-absorbent core 16 and may be bonded to each other inside the linear through-hole 21 though not shown.

A pair of the grooves 22, 23 continuously and rectilinearly extends substantially in parallel to the linear through-hole 21 in the direction along the longitudinal axis 11. These paired grooves 22, 23 do not extend through the liquid-absorbent core 16 in its thickness direction but are depressed from the lower surface 14.

The paired grooves 22, 23 have depth dimensions H2, H3 each of about 3 to 7 mm, preferably about 4 to 6 mm. The paired grooves 22, 23 have length dimensions L2, L3 as measured in the longitudinal direction along the longitudinal axis 11 each of about 110 to 140 mm, preferably about 120 to 135 mm which corresponds to about 30% of the length dimension L of the liquid-absorbent core 16 as measured in the direction along the longitudinal axis 11. These grooves 22, 23 are spaced apart from each other by a dimension P of about 50 to 85 mm, preferably about 60 to 80 mm.

As seen in FIG. 3, the liquid-absorbent pad is easily bowed and deformed along the linear through-hole 21 and the paired grooves 22, 23. Consequentially, the front region 15a exhibits a flexibility substantially higher than that exhibited by the rear region 15b.

The thickness dimension H of the liquid-absorbent core 16 and the width dimension W1 of the linear through-hole 21 may be selected in the manner as has been described to ensure that the opposed side edges of the linear through-hole 21 do not come in contact with each other even when the absorbent pad is bowed along the linear through-hole 21 as will be seen in FIG. 3. Thus a region of the absorbent pad destined to come in contact with the wearer's crotch region is reliably free from the presence of the liquid-absorbent core 16. Consequentially, the region of the absorbent pad destined to come in contact with the wearer's crotch region is adequately protected from remaining wet and therefore it is unlikely that the wearer might experience any uncomfortable feeling.

The absorbent pad can be made by the method of prior art. While the linear through-hole 21 can be formed, in the step of molding the liquid-absorbent core 16, by using steel stamp having a predetermined pattern so that the region containing no fluff pulp may be defined, it is also possible to form the linear through-hole 21 by die cutting the liquid-absorbent core 16 which has been molded. While the paired grooves 22, 23 can be formed by embossing the liquid-absorbent core 16 which has been molded, it is also possible to form these grooves 22, 23, in the step of molding the liquid-absorbent core 16, by using steel stamp having a predetermined pattern so that two regions being thinner than the remainder may be defined.

The absorbent pad can be more advantageously used in combination with disposable diapers or diaper covers or the other undergarments rather than being used independently and, in this case, it is not essential for the absorbent pad to be provided with fastener means to fasten the absorbent pad to the wearer's body.

Second Embodiment

Figure 4:
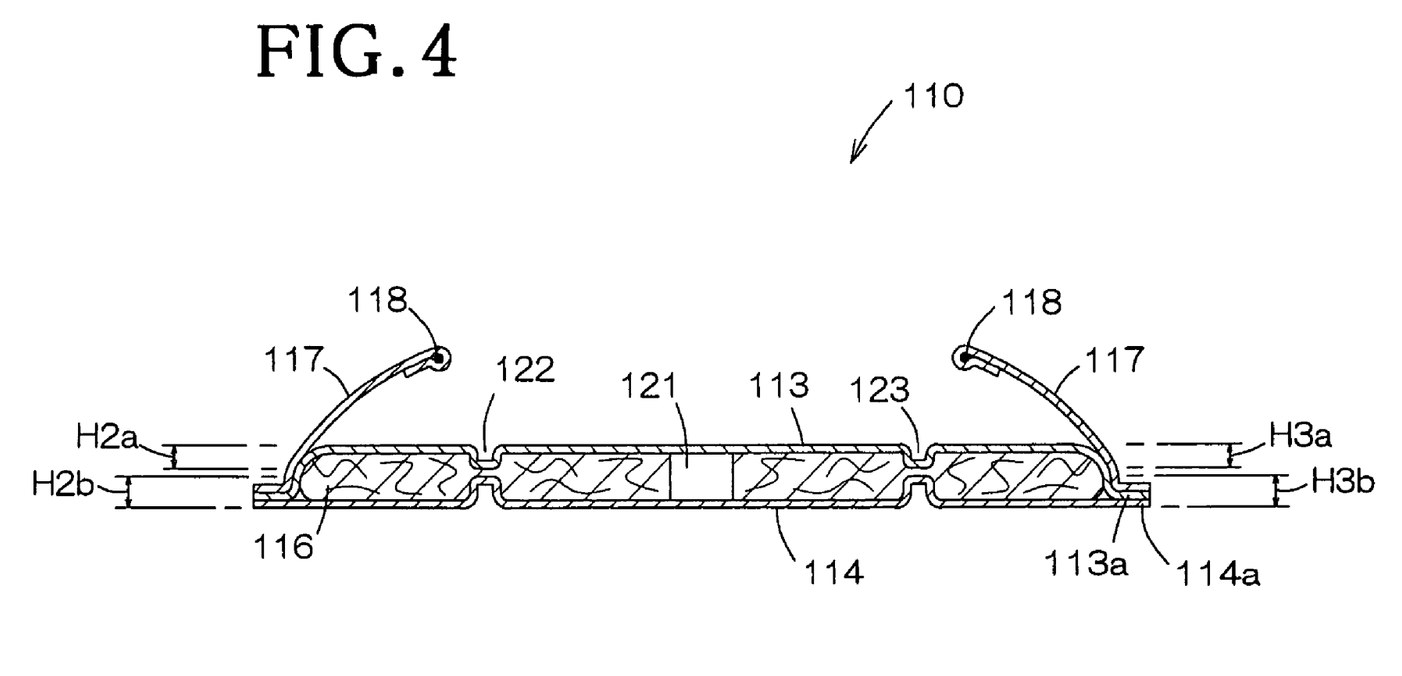
FIG. 4 is a sectional view similar to FIG. 2, showing a second embodiment of the absorbent pad according to this invention.

FIG. 4 is a sectional view similar to FIG. 2, showing a second embodiment of the absorbent pad according to this invention. Primary components/members as well as primary regions in the absorbent pad according to this second embodiment corresponding to those in the first embodiment are denoted by the same reference numerals as those in the first embodiment but added with 100, respectively, and details of them will not be repetitively described.

The absorbent pad according to the second embodiment is distinguished from the absorbent pad according to the first embodiment in that a pair of grooves 122, 123 is depressed not only from a lower surface 114 but also from an upper surface 113. The paired grooves 122, 123 are depressed from the upper surface 113 by depth dimensions H2a, H3a of preferably about 1.00 to 2.50 mm, respectively, and the paired grooves 122, 123 are depressed from the lower surface 114 by a depth dimensions H2b, H3b of preferably about 2 to 4 mm, respectively.

The paired grooves 122, 123 are depressed from both the upper surface 113 and the lower surface 114 and the depth dimension H2a, H3a of these grooves 122, 123 depressed from the upper surface 113 is smaller than the depth dimension H2b, H3b of these grooves 122, 123 depressed from the lower surface 114. Such dimensional relationship facilitates the absorbent pad to be deformed so that the side of the upper surface 113 may become convex and fit to the wearer's crotch region.

Third Embodiment

Figure 5:
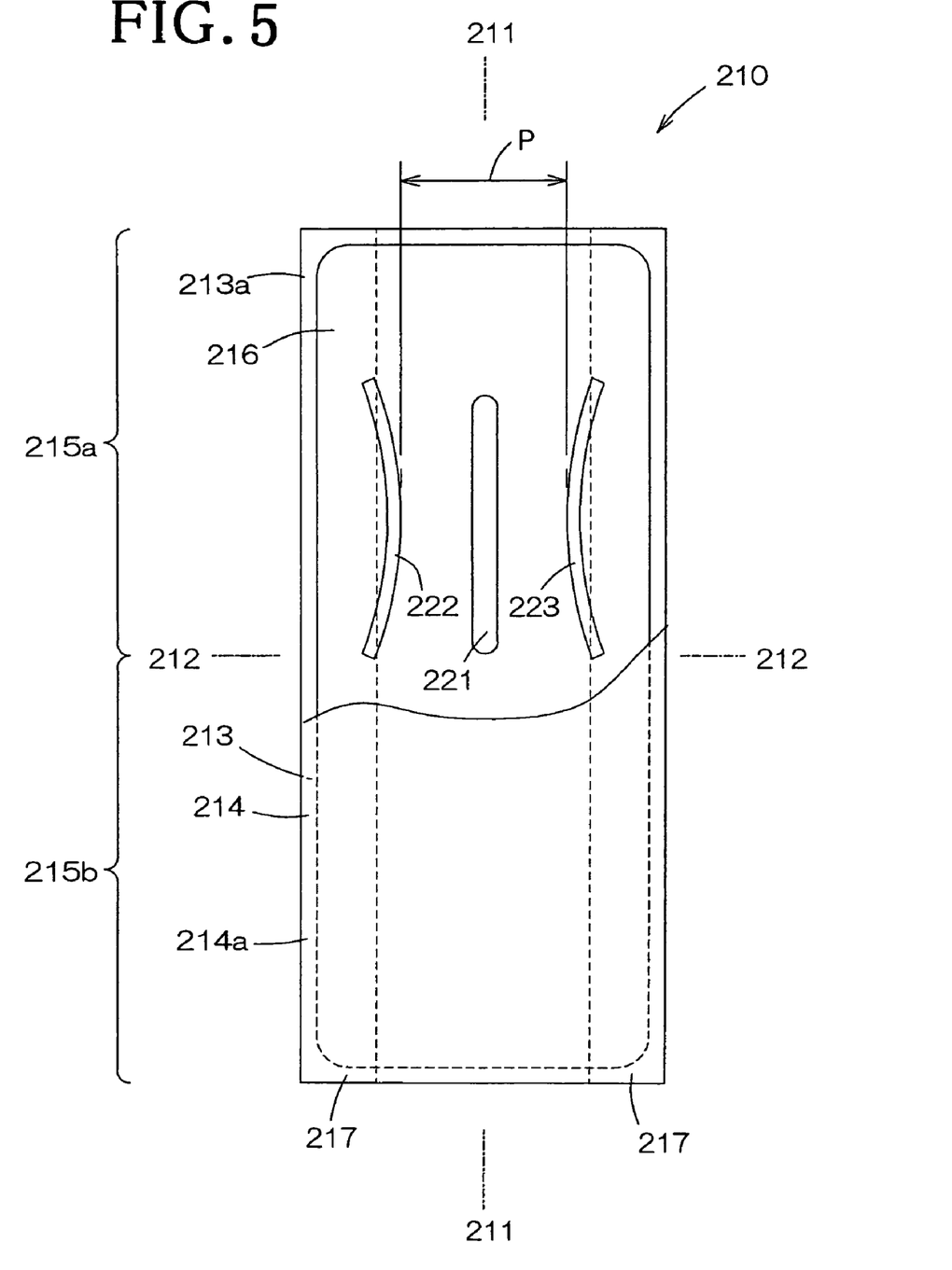
FIG. 5 is a partially cutaway plan view similar to FIG. 1, showing a third embodiment of the absorbent pad according to this invention.

FIG. 5 is a partially cutaway plan view similar to FIG. 1, showing a third embodiment of the absorbent pad according to this invention.

Primary components/members as well as primary regions in the absorbent pad according to this third embodiment corresponding to those in the first embodiment are denoted by the same reference numerals as those in the first embodiment but added with 200, respectively, and details of them will not be repetitively described.

The absorbent pad according to this third embodiment is distinguished from the absorbent pad according to the first embodiment in that a pair of grooves 222, 223 intermittently extends in the direction defined by a longitudinal axis 211 and describes circular arcs which are convex toward a linear through-hole 221. In this case, the shortest distance between the paired grooves 222, 223 is preferably about 60 to 80 mm.

The feature that these paired grooves 222, 223 describe circular arcs each convex toward the linear through-hole 221 ensures that the absorbent pad reliably fits to the wearer's crotch region.

Fourth Embodiment

Figure 6:
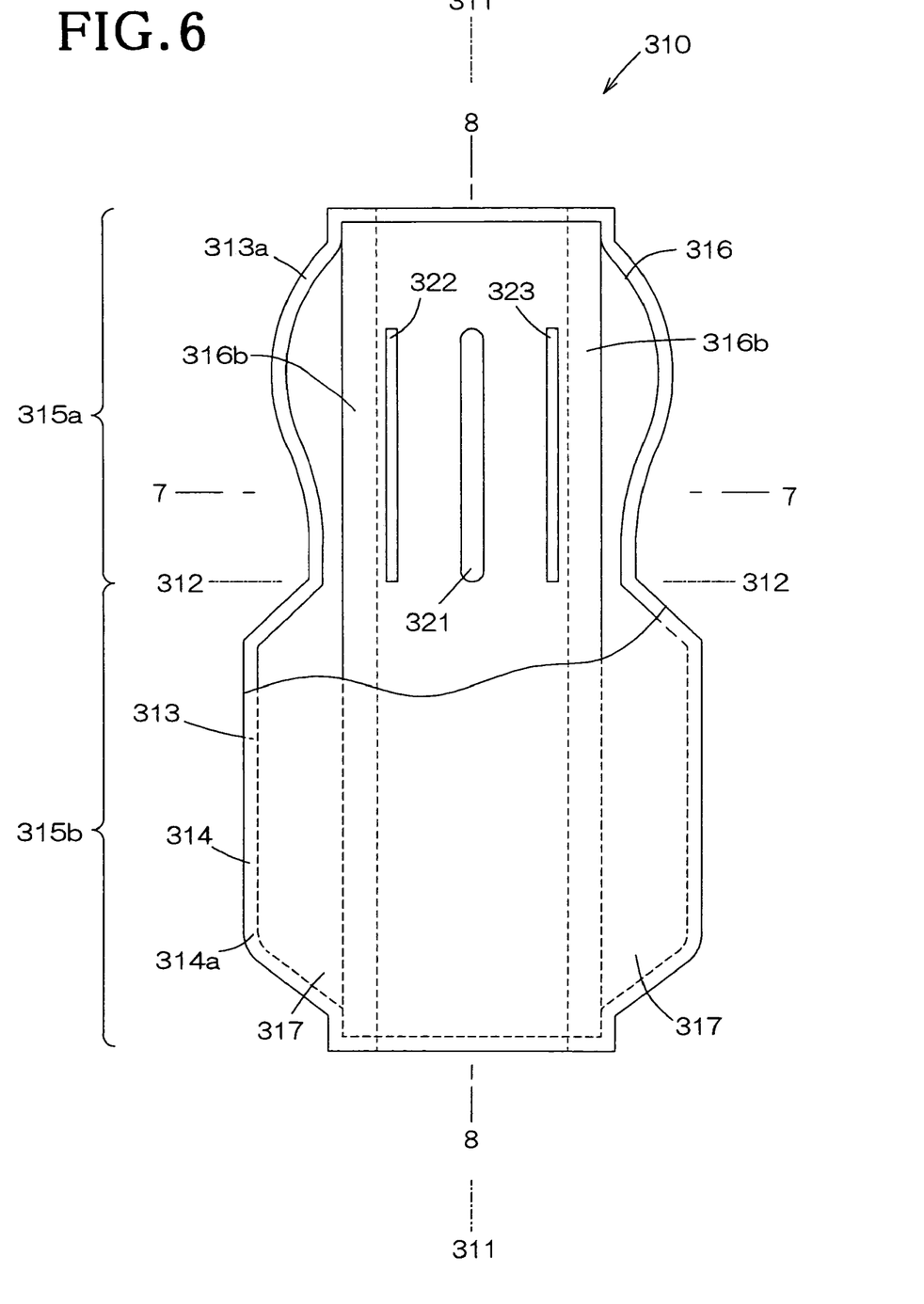
FIG. 6 is a partially cutaway plan view similar to FIG. 1, showing a fourth embodiment of the absorbent pad according to this invention.
Figure 7:
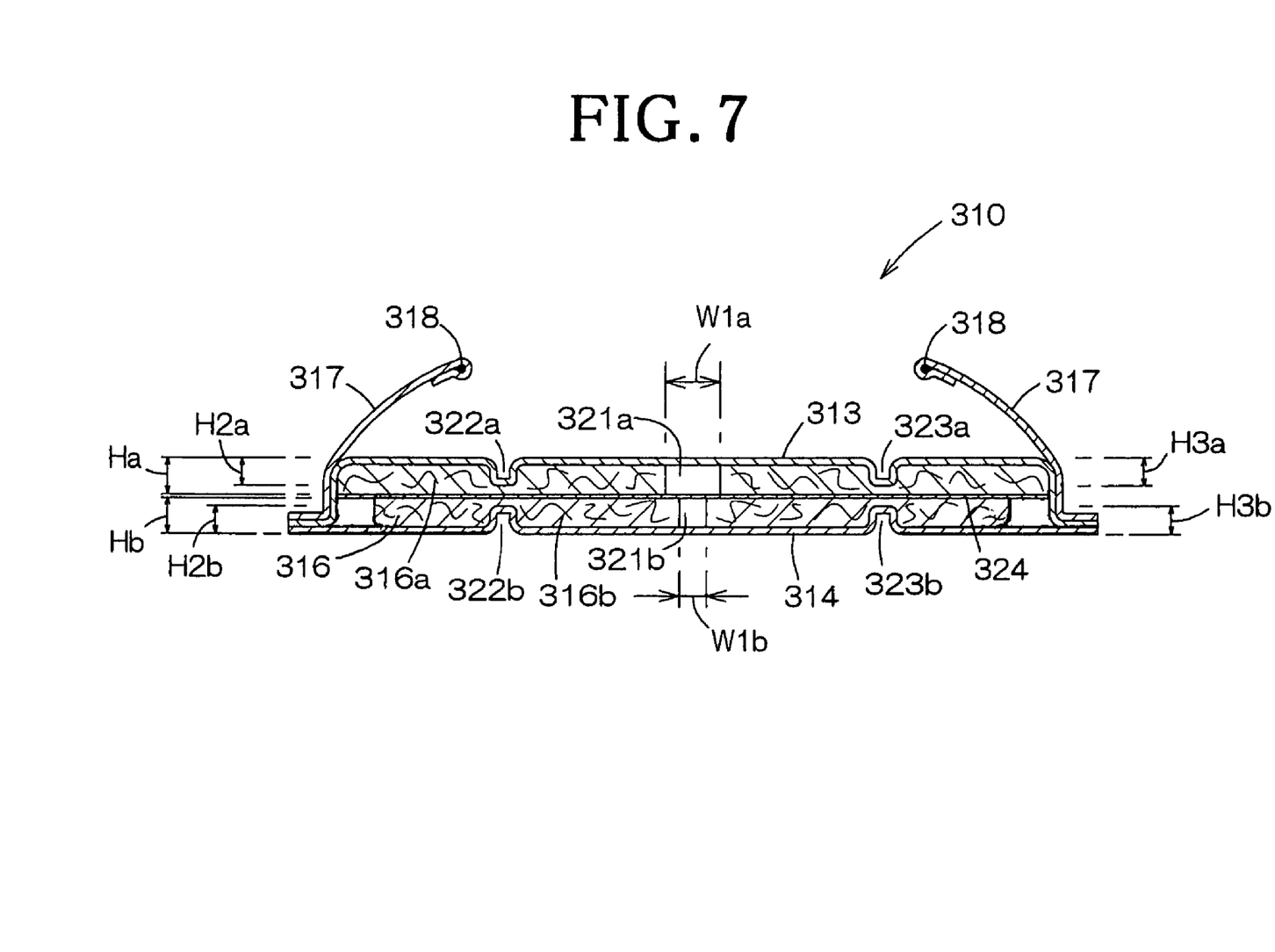
FIG. 7 is a sectional view taken along the line 7-7 in FIG. 6.
Figure 8:
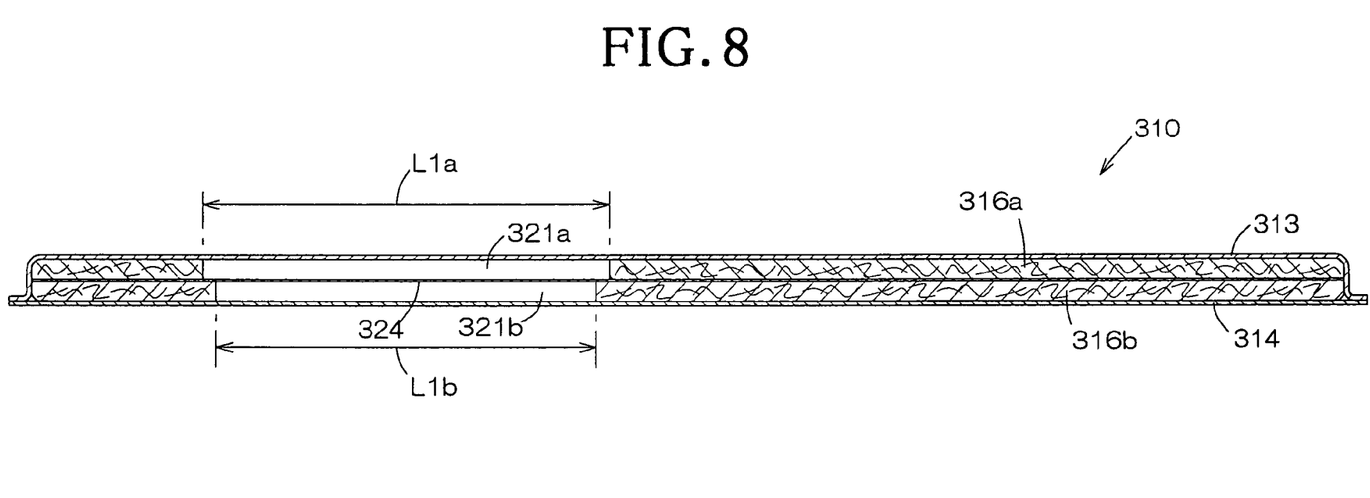
FIG. 8 is a sectional view taken along the line 8-8 in FIG. 6.
Figure 9:
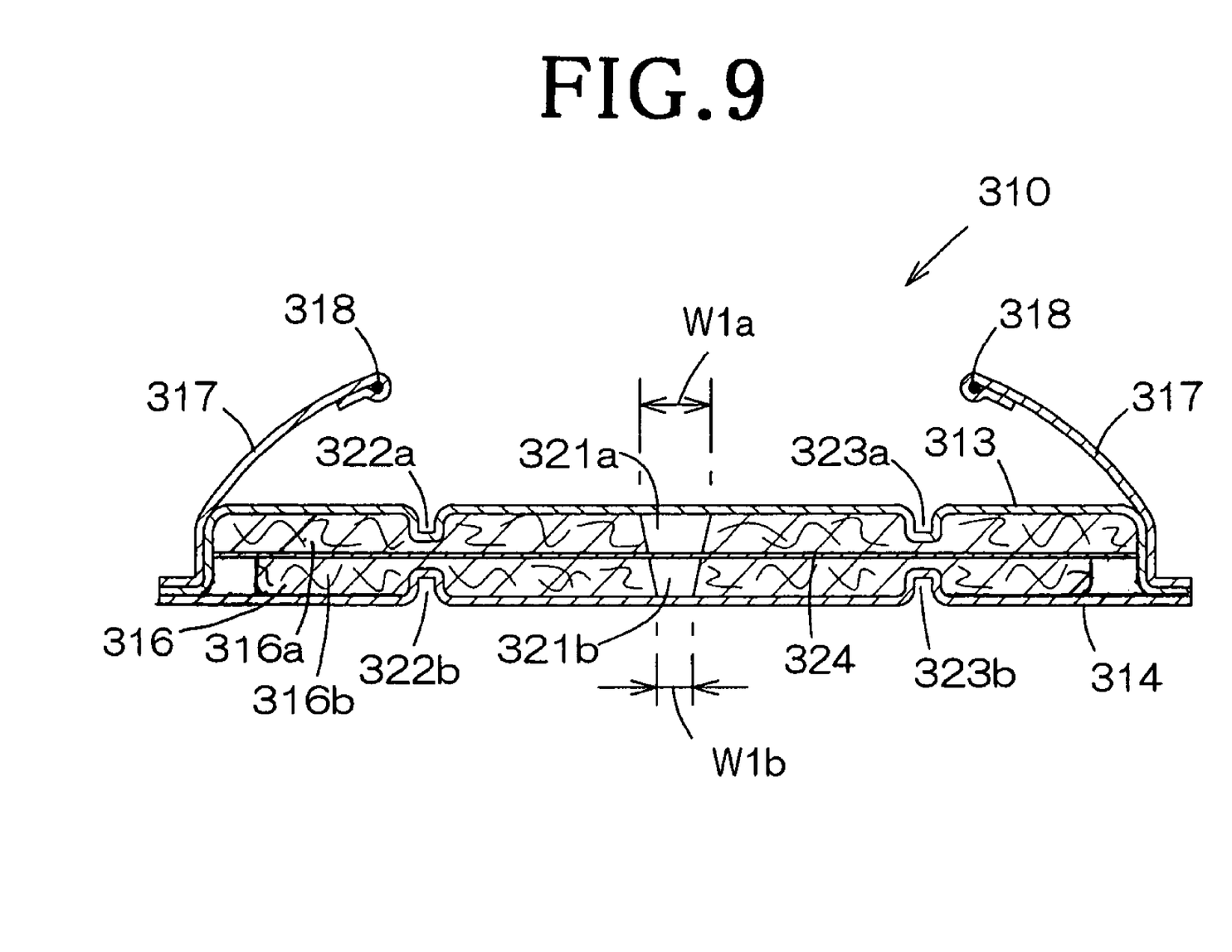
FIG. 9 is a sectional view similar to FIG. 7, showing further alternative embodiment of the absorbent pad according to this invention.

FIG. 6 is a partially cutaway plan view similar to FIG. 1, showing a fourth embodiment of the absorbent pad according to this invention. FIG. 7 is a sectional view taken along a line 7-7 in FIG. 6. FIG. 8 is a sectional view taken along a line 8-8 in FIG. 6. FIG. 9 is a sectional view similar to FIG. 7, showing further alternative embodiment of the absorbent pad according to this invention.

Primary components/members as well as primary regions in the absorbent pad according to this fourth embodiment corresponding to those in the first embodiment are denoted by the same reference numerals as those in the first embodiment but added with 300, respectively, and details of them will not be repetitively described.

The absorbent pad according to the fourth embodiment is distinguished from the absorbent pad according to the first embodiment in a construction as will be described.

As will be apparent from FIGS. 7 and 8, an absorbent fibrous structure 310 is a multi-layered structure and, more specifically, includes two-layered liquid-absorbent core 316 consisting of an upper layer core 316a and a lower layer core 316b. The upper layer core 316a has a gourd-like planar shape which is constricted in a substantially middle region thereof as viewed in the direction along a longitudinal axis 311. The lower layer core 316b has a substantially rectangular planar shape. A liquid-absorbent/diffusible sheet 324 such as a tissue paper is interposed between the upper layer core 316a and the lower layer core 316b. The liquid-absorbent/diffusible sheet 324 has a basis weight of approximately 10 to 30 g/m², preferably 15 to 20 g/m².

The upper layer core 316a and the lower layer core 316b are respectively provided substantially at the middle as viewed in the direction along the transverse axis with linear through-holes 321a, 321b and pairs of grooves 322a; 323a and 322b; 323b. The upper layer core 316a and the lower layer core 316b are overlapped together so that the respective linear through-holes 321a, 321b may be positioned in alignment with each other and the respective pairs of linear through-holes 322a; 323a and 322b; 323b may be positioned also in alignment with each other (See FIG. 7).

The upper layer core 316a has a thickness dimension Ha of preferably about 2.00 to 5.00 mm and the lower core 316b has a thickness dimension Hb of preferably about 2.500 to 5.500 mm. The grooves 322a, 323a depressed from an upper surface 313 of the upper layer core 316a have a depth dimension H2a of preferably 1.50 to 2.50 mm while the grooves 322b, 323b depressed from a lower surface 314 of the lower layer core 316b have a depth dimension H2b of preferably about 2.00 to 5.00 mm. A width dimension W1a of the linear through-hole 321a formed through the upper layer core 316a is different from a width dimension W1b of the linear through-hole 321b formed through the lower layer core 316b. Specifically, the width dimension W1a is preferably about 8 to 14 mm and the width dimension W1b is preferably about 6 to 12 mm (See FIG. 7). Similarly, a length dimension L1a of the linear through-hole 321a extending in the upper layer core 316a is different from a length dimension L1b of the linear through-hole 321b extending in the lower layer core 316b. Specifically, the length dimension L1a is preferably 110 to 140 mm and the length dimension L1b is preferably 90 to 120 mm (See FIG. 8).

The absorbent pad preferably exhibits a bending resistance along the paired grooves in a range of 10 to 70 g·cm as determined by Taper Method in accordance with JIS P8125. If the bending resistance is less than 10 g·cm, the absorbent pad will be excessively bent along the paired grooves and consequentially it will be difficult to achieve a desired deformation. If the bending resistance exceeds 70 g·cm, there is an anxiety that the wearer might experience a feeling of discomfort as the bent absorbent pad comes in contact with the wearer's crotch region.

While the linear through-holes 321a, 321b of the liquid-absorbent core 316 has step-like sectional shapes in the case of the embodiment shown in FIG. 7 (See FIG. 8 also), these linear through-holes 321a, 321b may be alternatively configured to have sectional shapes tapered from the upper surface 313 toward the lower surface 314.

The liquid-absorbent core 316 may be configured so as to have a gourd-like planar shape which is constricted in a substantially middle region thereof as viewed in the direction along a longitudinal axis 311 to ensure that a substantially middle region of the absorbent pad as viewed in the direction along the longitudinal axis 311 is reliably aligned with the narrowest region of the wearer's crotch region. In other words, the region of the absorbent pad adapted to be bent is reliably aligned with the wearer's crotch region.

The two-layered structure of the liquid-absorbent core 316, i.e., consisting of the upper layer core 316a and the lower core 316b advantageously facilitates it to make the liquid-absorbent core 316 in which the linear through-hole 321a and the paired grooves 322a, 323a on the side of the upper surface 313 respectively have the length dimension, the width dimension and the depth dimension different from those of the linear through-hole 321b and the paired grooves 322b, 323b on the side of the lower layer core 316b.

The two-layered liquid-absorbent core 316 in which the linear through-hole 321a on the side of the upper surface 313 is larger than the linear through-hole 321b on the side of the lower surface 314 is advantageous from a viewpoint as follows: even when some misalignment occurs in the course of overlapping the upper layer core 316a and the lower layer core 316b together, the size of the linear through-hole as viewed from the side of the upper surface 313 can be maintained to be substantially constant and the absorbent pad can fit to the deepest region of the wearer's crotch region. The step-like or tapered cross-sectional shapes given by the linear through-holes 321a, 321b of the liquid-absorbent core 316 advantageously contribute to enlargement in the surface area of the liquid-absorbent core 316 and thereby to improvement of bodily fluid absorbing capacity afforded by the absorbent pad.

The liquid-absorbent/diffusible sheet 324 interposed between the upper layer core 316a and the lower layer core 316b ensures that, upon reaching this sheet 324, bodily fluid spreads all over the liquid-absorbent core 316 without any apprehension that the liquid-absorbent core 316 might be locally saturated with bodily fluid.

The entire discloses of Japanese Patent Application No. 2004-286344 filed on Sep. 30, 2004 including specification, drawings and abstract are herein incorporated by reference in its entirety.

What is claimed is:

1. An absorbent pad, comprising:
    an absorbent fibrous structure having a longitudinal direction, a transverse direction perpendicular to the longitudinal direction, a first surface, a second surface opposite to said first surface, and front and rear regions successively arranged in the longitudinal direction, and
    a flexibility of said front region being higher than that of said rear region and defined at least by a first flexible region about which the absorbent fibrous structure is bendable,
    wherein
    the first flexible region comprises a through hole or groove which is longitudinally and continuously elongated along the longitudinal direction and which is present in the front region only, without extending into the rear region,
    the rear region defines about half of an entire length of the absorbent pad and is free of through-holes or grooves,
    the first flexible region is a central flexible region elongated along and located on a longitudinal center axis of the absorbent fibrous structure,
    the higher flexibility of said front region is further defined by second and third flexible regions about which the absorbent fibrous structure is bendable, and which are positioned exclusively in said front region on opposite sides of the first flexible region, and longitudinally and continuously elongated in the longitudinal direction without extending into the rear region, and
    said first flexible region comprises a linear through-hole extending through an entire thickness of said absorbent fibrous structure, and said second and third flexible regions comprise grooves depressed into the absorbent fibrous structure without extending through the entire thickness of said absorbent fibrous structure.

2. The absorbent pad as defined by claim 1, wherein the entire thickness of said absorbent fibrous structure is from 1 to 10 mm and said linear through-hole has a width in a range of 5 to 25 mm as measured in the transverse direction.

3. The absorbent pad as defined by claim 1, wherein an entire length of said linear though-hole as measured in the longitudinal direction corresponds to a range of 10 to 60% of an entire length of said absorbent fibrous structure as measured in the longitudinal direction.

4. The absorbent pad as defined by claim 3, wherein an entire length of each of said grooves as measured in the longitudinal direction corresponds to a range of 10 to 50% of the entire length of said absorbent fibrous structure as measured in the longitudinal direction.

5. The absorbent pad as defined by claim 1, wherein said grooves are depressed into the absorbent fibrous structure only from said second surface which is adapted to face away from a wearer's body, in use.

6. An absorbent pad, comprising:
an absorbent fibrous structure having a longitudinal direction, a transverse direction perpendicular to the longitudinal direction, a first surface, a second surface opposite to said first surface, and front and rear regions successively arranged in the longitudinal direction, and
a flexibility of said front region being higher than that of said rear region and defined at least by a first flexible region about which the absorbent fibrous structure is bendable,
wherein
the first flexible region comprises a through hole or groove which is longitudinally and continuously elongated along the longitudinal direction and which is present in the front region only, without extending into the rear region,
the rear region defines about half of an entire length of the absorbent pad and is free of through-holes or grooves,
the first flexible region is a central flexible region elongated along and located on a longitudinal center axis of the absorbent fibrous structure,
the higher flexibility of said front region is further defined by second and third flexible regions about which the absorbent fibrous structure is bendable, and which are positioned exclusively in said front region on opposite sides of the first flexible region, and longitudinally and continuously elongated in the longitudinal direction without extending into the rear region, and
said second flexible region and third flexible region are spaced from each other, in the transverse direction, by a dimension in a range of 60 to 90 mm.

7. An absorbent pad, comprising:
an absorbent fibrous structure having a longitudinal direction, a transverse direction perpendicular to the longitudinal direction, a first surface, a second surface opposite to said first surface, and front and rear regions successively arranged in the longitudinal direction, and
a flexibility of said front region being higher than that of said rear region and defined at least by a first flexible region about which the absorbent fibrous structure is bendable,
wherein
the first flexible region comprises a through hole or groove which is longitudinally and continuously elongated along the longitudinal direction and which is present in the front region only, without extending into the rear region,
the rear region defines about half of an entire length of the absorbent pad and is free of through-holes or grooves,
the first flexible region is a central flexible region elongated along and located on a longitudinal center axis of the absorbent fibrous structure,
the higher flexibility of said front region is further defined by second and third flexible regions about which the absorbent fibrous structure is bendable, and which are positioned exclusively in said front region on opposite sides of the first flexible region, and longitudinally and continuously elongated in the longitudinal direction without extending into the rear region, and
said first flexible region comprises a through-hole extending through an entire thickness of said absorbent fibrous structure, and each of said second and third flexible regions comprises at least one groove depressed into the absorbent fibrous structure without extending through the entire thickness of said absorbent fibrous structure.

8. The absorbent pad as defined by claim 7, wherein said at least one groove is depressed only from said second surface which is hydrophobic and adapted to face away from a wearer's body, in use.

* * * * *